(12) United States Patent
Iwasawa et al.

(10) Patent No.: US 10,730,043 B2
(45) Date of Patent: Aug. 4, 2020

(54) SAMPLE COLLECTION AND SEPARATION DEVICE

(71) Applicant: MBS CO., LTD., Tokyo (JP)

(72) Inventors: Hajime Iwasawa, Tokyo (JP); Tomoaki Nishimura, Tokyo (JP); Shota Nemoto, Tokyo (JP); Masayoshi Nakai, Tokyo (JP)

(73) Assignee: Micro Blood Science Inc., Tokyo (JP)

( * ) Notice: Subject to any disclaimer, the term of this patent is extended or adjusted under 35 U.S.C. 154(b) by 93 days.

(21) Appl. No.: 15/558,993

(22) PCT Filed: Feb. 9, 2016

(86) PCT No.: PCT/JP2016/053776
§ 371 (c)(1),
(2) Date: Aug. 21, 2018

(87) PCT Pub. No.: WO2016/147748
PCT Pub. Date: Sep. 22, 2016

(65) Prior Publication Data
US 2018/0345276 A1    Dec. 6, 2018

(30) Foreign Application Priority Data

Mar. 17, 2015 (JP) .................................. 2015-054065
Jul. 13, 2015 (WO) ................... PCT/JP2015/069992

(51) Int. Cl.
*G01N 1/00*     (2006.01)
*B01L 3/00*     (2006.01)
(Continued)

(52) U.S. Cl.
CPC ...... *B01L 3/5021* (2013.01); *A61B 5/150022* (2013.01); *A61B 5/150099* (2013.01);
(Continued)

(58) Field of Classification Search
CPC ........................................................ G01N 1/00
See application file for complete search history.

(56) References Cited

U.S. PATENT DOCUMENTS 3,139,121 A * 6/1964 Ballin ................ B65D 51/2857
                                                        141/24
3,914,985 A    10/1975 von Behrens
(Continued)

FOREIGN PATENT DOCUMENTS

EP    0971231 A1    1/2000
JP    S61203965 A   9/1986
(Continued)

OTHER PUBLICATIONS

Extended European Search Report dated Dec. 22, 2017 for European Patent Application No. 16764579.5.
(Continued)

*Primary Examiner* — Jyoti Nagpaul
(74) *Attorney, Agent, or Firm* — Hunton Andrews Kurth LLP

(57) ABSTRACT

Provided is a sample collection and separation device comprising a sample collection unit having a sample collection portion that uses capillary action and an analyte storage unit having a housing into which the sample collection unit is inserted, whereby the sample collection unit containing the collected sample is integrated by means of insertion, so as to permit centrifugation and storage or transport of the sample, and the target sample can be recovered following centrifugation.

18 Claims, 7 Drawing Sheets

(51) Int. Cl.
    *A61B 5/15*     (2006.01)
    *G01N 1/10*    (2006.01)
    *G01N 33/48*   (2006.01)

(52) U.S. Cl.
    CPC .. *A61B 5/150305* (2013.01); *A61B 5/150343* (2013.01); *A61B 5/150351* (2013.01); *B01L 3/502* (2013.01); *B01L 3/50825* (2013.01); *G01N 1/00* (2013.01); *G01N 1/10* (2013.01); *G01N 33/48* (2013.01); *A61B 5/150755* (2013.01); *A61B 5/150786* (2013.01); *B01L 2200/06* (2013.01); *B01L 2200/10* (2013.01); *B01L 2200/18* (2013.01); *B01L 2300/042* (2013.01); *B01L 2300/046* (2013.01); *B01L 2300/06* (2013.01); *B01L 2300/0609* (2013.01); *B01L 2300/0838* (2013.01); *B01L 2300/0851* (2013.01); *B01L 2400/0406* (2013.01)

(56) References Cited

U.S. PATENT DOCUMENTS

| | | |
|---|---|---|
| 4,007,639 A | 2/1977 | Haeckel |
| 4,769,025 A | 9/1988 | Sarstedt et al. |
| 5,506,145 A | 4/1996 | Bull et al. |
| 5,556,598 A | 9/1996 | Raybuck et al. |
| 5,980,734 A | 11/1999 | Itoh |
| 2002/0064484 A1 | 5/2002 | Lin et al. |
| 2003/0108447 A1 | 6/2003 | Yokoi et al. |
| 2006/0229530 A1 | 10/2006 | Hosoda et al. |
| 2007/0161491 A1 | 7/2007 | Jinno et al. |
| 2013/0225387 A1 | 8/2013 | Hirai et al. |
| 2015/0003140 A1 | 1/2015 | Funane et al. |
| 2016/0245729 A1 | 8/2016 | Yamakawa et al. |

FOREIGN PATENT DOCUMENTS

| | | |
|---|---|---|
| JP | H01156747 U | 10/1989 |
| JP | H0230555 A | 1/1990 |
| JP | 02305554 A | 12/1990 |
| JP | H08-166389 A | 6/1996 |
| JP | H09141135 A | 6/1997 |
| JP | H09304398 A | 11/1997 |
| JP | 10010121 A | 1/1998 |
| JP | H10243940 A | 9/1998 |
| JP | 2000074910 A | 3/2000 |
| JP | 2001235466 A | 8/2001 |
| JP | 2002082112 A | 3/2002 |
| JP | 2005017281 A | 1/2005 |
| JP | 2006288680 A | 10/2006 |
| WO | 2012063877 A1 | 5/2012 |
| WO | 2013098792 A1 | 7/2013 |
| WO | 2015034009 A1 | 3/2015 |

OTHER PUBLICATIONS

International Search Report and Written Opinion dated Apr. 26, 2016 in PCT application No. PCT/JP2016/053776.
Communication pursuant to Article 94(3) EPC dated Jul. 27, 2018 for European national phase application No. 16764579.5.

* cited by examiner

SAMPLE COLLECTION AND SEPARATION DEVICE

CROSS REFERENCE TO RELATED APPLICATIONS

The present application is a National Stage Application of PCT/JP2016/053776, filed Feb. 9, 2016, which claims priority to JP2015-054065, filed on Mar. 17, 2015 and PCT/JP2015/069992, filed on Jul. 13, 2015.

FIELD OF THE INVENTION

The present invention relates to a device for collecting a very small amount of a sample. Particularly, the present invention relates to a collection and separation device which is used for collection of body fluid and separation thereof.

BACKGROUND OF THE INVENTION

It is known that condition changes and diseases in the living body appear in variations of body fluid, for example, blood, urine, saliva and the like as biological reactions. Then, a change in physical condition is monitored and diseases are detected, by measuring and analyzing components contained in body fluid.

Particularly, blood tests measuring blood components are widely conducted as an effective means for investigating diseases and as a means for health management.

In measuring a component in body fluid, it is required to reliably collect a necessary amount of body fluid. For example, in a collection instrument having a body fluid collecting part, a developing part thereof and a determining part thereof disposed so as to connect sequentially on a plate-like base, body fluid collected by the collecting part is introduced to the determining part through the developing part. Further, a collection instrument in which an absorbing part, a liquid retaining part, and in some cases, further a recovering part are disposed sequentially on a hydrophilic absorbent is also suggested. In these body fluid collection instruments, body fluid is collected by allowing an absorbent composed of fiber to absorb body fluid. In these collection instruments, blood absorbed by the absorbent is not separated and specific components are analyzed and determined at the determining part, alternatively, the absorbent having absorbed blood is immersed in separating liquid, then, plasma is separated from the absorbent and specific components are analyzed. The former means is not suitable for analysis of arbitrary components in serum or plasma. In the latter means, an operation for obtaining plasma components is complicated. In addition, the amount of a specific component in blood cannot be measured correctly in either method.

In addition, there is a suggestion on a micro blood sampling tool using a disposable pipette in which a dropper tube and a flexible cap communicate (Patent document 1). In this blood sampling tool, liquid is temporarily sucked, then, the sucked liquid can be released, but the collected blood cannot be kept under the same state, thus, the liquid cannot be preserved and separated.

Further, a blood collection kit comprises a blood collecting tool and a blood collecting bottle is suggested (Patent document 2). This blood collecting tool is composed of a cylindrical liquid absorbing unit for performing temporal liquid absorption disposed at the end and containing blood coagulation preventing liquid and a pushing unit which pushes the rear surface of the liquid absorbing unit to separate the liquid absorbing unit, while, a chemical solution is contained in the blood collecting bottle. When the pushing unit of the blood collecting tool is pushed and the blood collecting tool is pushed into the blood collecting bottle, blood is eluted from the end of the blood collecting tool into the chemical solution. Since the collected blood is mixed in the chemical solution, however, plasma of the collected blood cannot be separated, and additionally, the amount of a specific component in the blood cannot be measured correctly.

The blood test using serum derived from collected blood includes conventionally operations such as blood collection using a syringe with needle and a blood collecting tube, and according to circumstances, transfer to a centrifugal separation vessel, centrifugation, serum suction, and application of the sucked serum to an automated analyzer.

However, blood collection by a syringe needle places a heavy burden such as strong pain and the like on a person to be blood-collected. Particularly in infants and elderly people, and not healthy people, blood collection is difficult in some cases, since blood vessel is narrow, and correct tapping of a syringe needle into blood vessel from the outside is difficult, and the like.

Since blood test with a very small amount of blood has become possible recently, conventional blood collecting methods using a syringe with needle and a blood collecting tube have a problem that unnecessarily large amount of blood is collected to force a person to be blood-collected an excessive burden and most of the collected blood is not necessary for the examination.

In contrast, a currently suggested blood collection instrument for collecting a very small amount of blood has a problem that preparation of serum or plasma suitable for use in the later blood test like in the conventional blood collecting method using a syringe with needle and a blood collecting tube is impossible.

As an instrument for collecting a very small amount of peripheral blood, a blood collecting tube composed of a capillary tube is conventionally known. Further, a tube having a cylinder-like structure having a nozzle portion in the form of a capillary tube is suggested, in which blood held in a capillary tube is easily taken out without transferring blood collected in a capillary tube to a reservoir (Patent document 3). In this technology, a cap for plugging the nozzle portion in the form of a capillary tube is prepared, the nozzle of a capillary tube is plugged using the cap after collecting blood, and it is placed in an outer vessel in the form of a cylinder. Alternatively, a cap structure for the nozzle is prepared in the outer vessel, and when the capillary tube is inserted into the outer vessel, the nozzle is plugged. Under this state, centrifugation and transfer are possible.

An instrument using a capillary tube is suggested as a blood collection instrument causing a small amount of blood collection, however, the collected blood is subjected to a centrifugal treatment thereafter.

In the blood collection instrument as suggested in Patent document 3, when centrifugation is conducted, respective fractions of blood cells and serum are constantly in contact at the liquid level, and for example, glucose contained in serum is consumed as a nutrient material of red blood cells, thus, if transportation takes a long period of time, correct quantification becomes difficult. That is, measurement should be carried out immediately after blood collection, thus, this instrument is not suitable for storage and preservation.

Furthermore, though blood test with a very small amount of blood has become possible as described above, the amount of a sample required should vary depending on conditions such as target test items, apparatus and reagents to be used, thus, collecting amount should be changed depending on conditions, for conducting blood collection of an optimum amount while avoiding blood collection of unnecessarily large amount.

CITATION LIST

Patent Literature

[Patent Literature 1] Japan Unexamined Patent Application Publication No. 2005-017281
[Patent Literature 2] Japan Unexamined Patent Application Publication No. 2006-288680
[Patent Literature 3] U.S. Pat. No. 4,007,639

SUMMARY OF THE INVENTION

Technical Problem

The present invention has an object of providing a device capable of collecting a very small amount of a sample in a state suitable for later testing even when a very small amount of a sample is collected, in consideration of the above-described problem. Further, the present invention has an object of providing a device capable of collecting a sample in an amount and a state suitable for later blood test even when a very small amount of peripheral blood is a sample. Still further, the present invention has an object of providing a device of collecting a very small amount of peripheral blood for performing accurate measurement, using a conventional reagent and analysis apparatus.

Solution to Problem

In a test using blood as a sample, preparation of a sample by centrifugation is conducted depending on the object, however, in the present specification, the supernatant component obtained by centrifuging the whole blood sample is defined as serum and the supernatant component obtained in the condition of addition of an anticoagulant is defined as plasma. Further, the precipitate component generated by centrifugation conducted to obtain serum or plasma is defined as blood cell.

One embodiment of the sample collection and separation device according to the present invention has a sample collection unit having an inside with a space for holding a sample and having openings at the top and the bottom, an analyte storage unit having a bottom cap for sample collection unit tightly sealing the bottom opening of the sample collection unit and having a housing means into which the sample collection unit is insertable, and an analyte sealing cap for plugging the top opening of the sample collection unit. In the inside space of the sample collection unit, the bottom opening and the top opening communicate, and the inner diameter thereof increases (preferably, gradually) from the bottom opening toward the top opening. In the sample collection and separation device according to the present invention, when the analyte sealing cap plugs the top opening of the sample collection unit under condition of insertion of the sample collection unit into the analyte storage unit, a sample is stored under sealed state. By this, preservation and/or transportation of the collected sample (analyte) can be conducted easily under this condition. In a more preferable embodiment, when the sealing cap of the analyte storage unit plugs the top opening of the sample collection unit under condition of insertion of the sample collection unit into the analyte storage unit, pressure is applied to the sample collection unit from the top, sealing of the bottom opening of the sample collection unit by the bottom cap provided in the analyte storage unit becomes more complete, and the sample sealed condition becomes better. By this, preservation and/or transportation of the collected sample (analyte) can be conducted more safely and easily.

In another embodiment of such a sample collection and separation device according to the present invention, the wall surface defining the inside space into which a sample is placed of the above-described sample collection unit forms a gradient continuing from the bottom opening toward the top opening.

In another embodiment of such a sample collection and separation device according to the present invention, the above-described bottom cap for the sample collection unit has an agent holding portion for holding an agent in a part thereof, and it is configured that when the sample collection unit is inserted into the analyte storage unit and the bottom opening is inserted into the agent holding portion, then, at least a part of the agent enters the sample collection unit.

In another embodiment of such a sample collection and separation device according to the present invention, the surface of the wall defining the inside space into which a sample is placed is hydrophilized.

In another embodiment of such a sample collection and separation device according to the present invention, the bottom cap further has a lock mechanism, and when the bottom opening of the sample collection unit is inserted into the agent holding portion, the lock mechanism contacts the end peripheral part of the sample collection unit, and a sample is held sealed under condition of entering of at least a part of the agent into the sample collection unit.

In any of the sample collection and separation devices described above according to the present invention, the analyte sealing cap can be integrated with the sample collection unit or the analyte storage unit.

The above-described sample can be collected through the bottom opening of the sample collection unit by utilizing capillary action or negative pressure generated by flow of fluid. For example, in the case of collection of peripheral blood from fingertip or earlobe, fingertip or earlobe is tapped, then, the bottom opening of the sample collection unit is brought into contact with blood coming out, thereby, blood is introduced into the sample collection unit by capillary action or negative pressure generated by flow of fluid, thus, the unit can collect blood.

In collection of a sample, an amount of sample collected by the sample collection unit is not limited, and the amount of a sample to be collected can be changed depending on objects, including an apparatus or an agent to be used, and examination items and the like. When the sample collection and separation device of the present invention is used, a very small amount of a sample (for example, blood) can be collected in any amount, for example, any amount from 10 µL to 200 µL.

The internal diameter increases from the bottom opening toward the top opening in the sample collection unit of the present invention, and in a particularly preferable case, a portion extending from the bottom opening toward upper direction in the sample collection unit and holding a sample after collection (hereinafter, referred to as "sample holding portion" in the present specification) forms a pipette tip shape in which its internal diameter increases continuously (for example, a portion holding a sample 11 shown in FIG.

7). The volume of the sample holding portion is preferably 200 μL or less, more preferably 150 μL or less, further preferably 100 μL or less.

It is preferable that the inner wall of the sample holding portion is hydrophilized. When the inner wall is hydrophilized, flow of a sample is smooth even if a highly viscous sample such as blood and the like is collected. As a result, even when blood is collected through the bottom opening, a target amount of blood can be easily collected by a combination of capillary action with an effect of hydrophilization of the inner wall.

The sample collection and separation device according to the present invention can be preserved and/or transported under condition of insertion of the sample collection unit containing a sample into the analyte storage unit. For example, when blood is used as a sample, the sample collection and separation device according to the present invention can be preserved and/or transported under condition of charging of blood into the device.

The sample collection and separation device according to the present invention can be subjected to a centrifugation under condition of insertion of the sample collection unit into the analyte storage unit. By this, the sample collection and separation device according to the present invention in the condition of holding a sample (analyte) therein can be subjected to centrifugation to attain separation into the supernatant (serum or plasma, in the case of blood) and the precipitate (blood cell, in the case of blood), and can be preserved and/or transported as it is.

Further, in the sample collection and separation device according to the present invention, an agent such as an anticoagulant or a separating agent depending on a target sample such as serum or plasma can be previously added into the device before collecting blood. That is, when the sample collection unit having collected a sample is inserted into the analyte storage unit, a separating agent flows into the sample collection unit, then, the end portion of the sample collection unit is sealed. By this, a sample containing the agent added can be prepared without separately adding the agent.

In the sample collection and separation device according to the present invention, the analyte sealing cap is opened after carrying out a centrifugation operation, and the resultant supernatant (serum or plasma, in the case of blood) can be collected by a collection means (for example, micro pipette).

Further, the upper part of the inside space of the sample collection unit can also be formed into an inverse conical shape, and by this, the collection means can easily access into the sample collection unit.

As the sample, body fluid, for example, blood, lymph, saliva, urine or tissue fluid can be used, but the sample is not limited to them. Blood can be preferably used, and peripheral blood can be particularly preferably used.

Advantageous Effect of the Invention

A very small amount of body fluid such as blood and the like can be collected in any amount without waste, and centrifugation of body fluid is possible for an improvement in inspection accuracy, by using the sample collection and separation device of the present invention.

According to the sample collection and separation device of the present invention, for example, even 200 μL or less of a sample can be easily collected in a hollow structure in the sample collection and separation device, and by centrifuging the collected sample as it is without transferring to another vessel or the like, body fluid can be recovered without waste. For example, when blood is used as a sample, serum or plasma and blood cells can be recovered without waste.

When the sample collection and separation device of the present invention is used, accurate measurement can be conducted using a very small amount of peripheral blood as a sample by using conventional reagents and a analysis apparatus.

DESCRIPTION OF EMBODIMENT

The sample collection and separation device and the sample collection method and separation method according to embodiments of the present invention will be illustrated below referring to drawings, using examples using blood as a biological sample which requires centrifugation for examination. In the following explanations, peripheral blood is used, however, the sample collection and separation device of the present invention can also be used as a micro collection and storage vessel for other biological samples not requiring centrifugation.

First Embodiment

Figure 1:
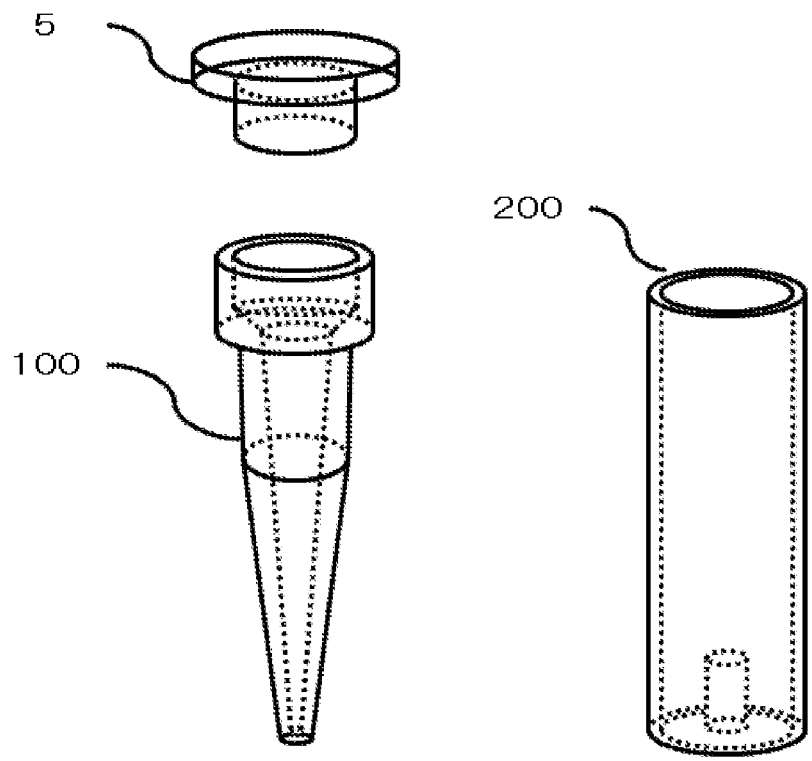
FIG. 1 is a view showing the configuration of a first embodiment of the sample collection and separation device according to the present invention.

FIG. 1 is a view showing a first embodiment of a sample collection and separation device 300 of the present invention, and comprises a sample collection unit 100, an analyte storage unit 200 and an analyte sealing cap 5.

The sample collection and separation device 300 of the first embodiment according to the present invention will be illustrated below using FIG. 2.

Figure 2:
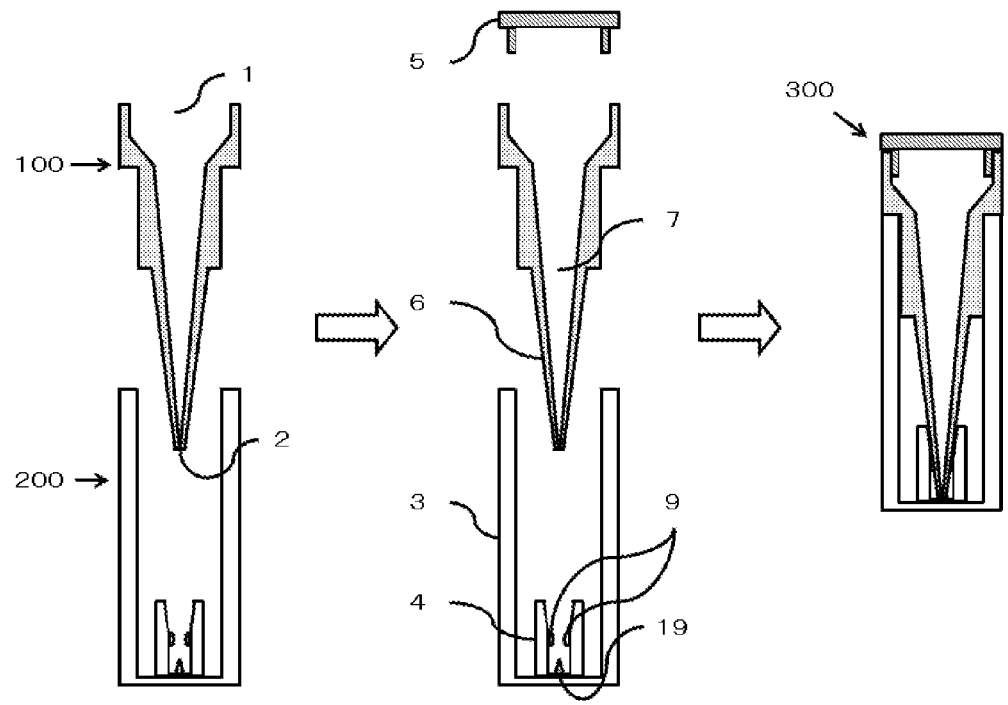
FIG. 2 is a view showing a schematic plan view of the sample collection and separation device of the first embodiment comprising the sample collection unit and the analyte storage unit according to the present invention, and showing the way of using the sample collection unit and the analyte storage unit.

As shown in FIG. 2, the sample collection and separation device 300 comprises the sample collection unit 100, the analyte storage unit 200 and the analyte sealing cap 5. The analyte storage unit 200 comprises an analyte storage unit main body 3 and a sample collection unit bottom cap 4. The bottom cap 4 may be integrated with the analyte storage unit main body 3. The analyte sealing cap 5 may be partially integrated so as to be connected with the sample collection unit 100 or the analyte storage unit 200.

The sample collection unit 100 and the analyte storage unit main body 3 can be fitted by insertion, and the inserted sample collection unit 100 is held by the bottom cap 4 provided at the bottom of the analyte storage unit main body 3 and a bottom opening 2 of the sample collection unit 100 is sealed.

For the analyte storage unit main body 3 carrying the sample collection unit 100 inserted therein, a sample in the sample collection unit is sealed by the bottom cap 4 and the analyte sealing cap 5, and centrifugation and storage or transportation thereof are possible. In the figure, a lock mechanism 9 and a protrusion 19 are provided in the bottom cap, but, they may be present or absent.

Second Embodiment

Figure 3:
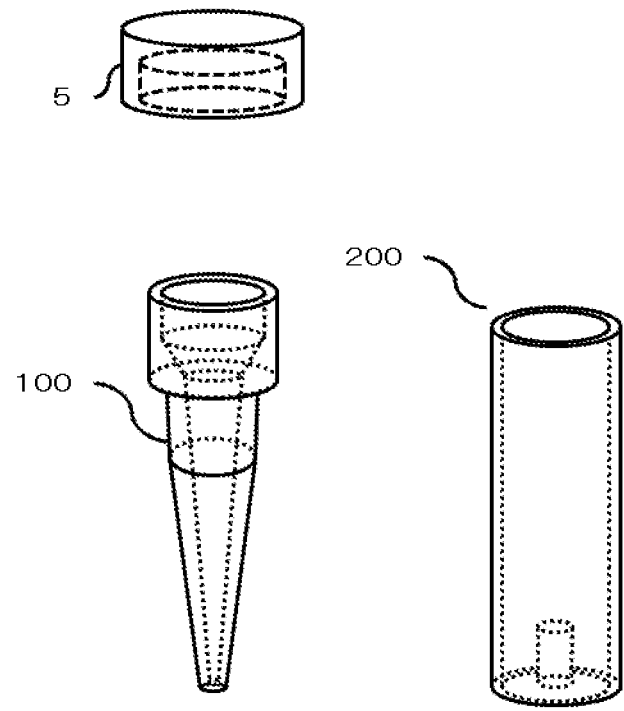
FIG. 3 is a view showing the configuration of a second embodiment of the sample collection and separation device according to the present invention.
Figure 4:
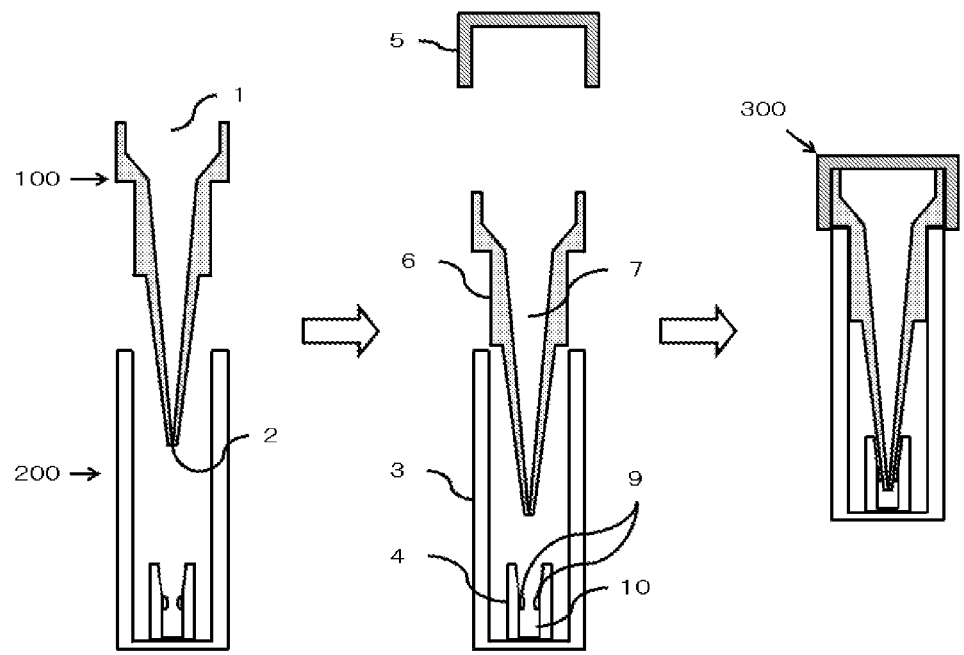
FIG. 4 is a view showing a schematic plan view of the sample collection and separation device of the second embodiment comprising the sample collection unit and the analyte storage unit according to the present invention, and showing the way of using the sample collection unit and the analyte storage unit.

FIG. 3 is a view showing a second embodiment of the sample collection and separation device 300 of the present invention. FIG. 4 is a view explaining a sample collection and separation instrument 300 using the second embodiment. Like in the first embodiment, for the analyte storage unit main body 3 carrying the sample collection unit 100 inserted therein, a sample in the sample collection unit is sealed by the sample collection unit bottom cap 4 and the analyte sealing cap 5, and centrifugation and storage or transportation thereof are possible. In this situation, sealing of the bottom opening of the sample collection unit is attained by close adhesion of the end peripheral part of the sample collection unit with the inner side of the bottom cap 4, and also in the second embodiment, sealing of the opening may be attained by close adhesion of the end of the sample collection unit with the basal plane of the bottom cap, like in the first embodiment. In the figure, the numeral 10 represents an agent holding portion and the numeral 9 represents a lock mechanism. When an agent is previously provided in an agent holding portion, the lock mechanism 9 is preferably provided.

Third Embodiment

Figure 5:
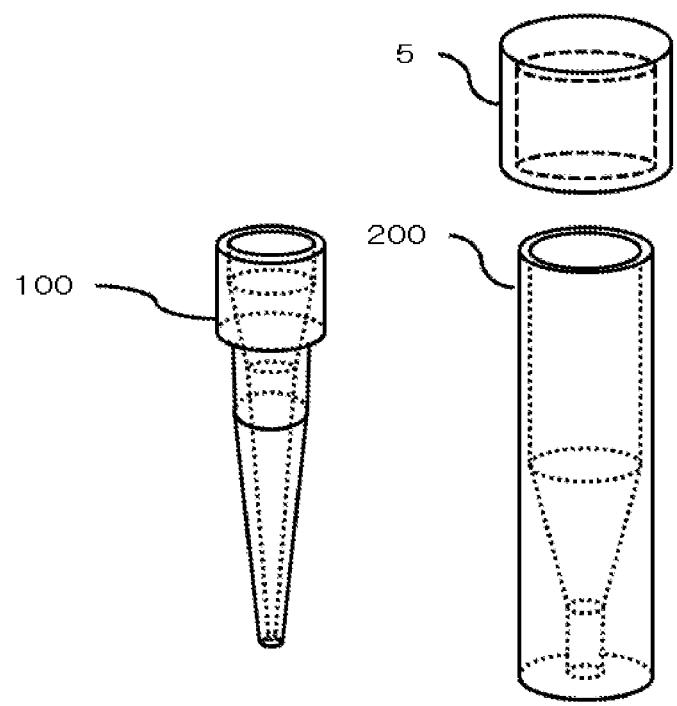
FIG. 5 is a view showing the configuration of a third embodiment of the sample collection and separation device according to the present invention.

FIG. 5 is a view showing a third embodiment of the sample collection and separation device 300 of the present invention. The bottom cap 4 for the sample collection unit is integrated with the analyte storage unit main body 3, and an agent holding portion 10 in which an agent can be added according to the collection condition is formed so as to be provided on the base. Also, the sealing cap 5 is formed so that it can seal the analyte storage unit main body 3, irrespective of insertion or no insertion of the sample collection unit 100.

Figure 6:
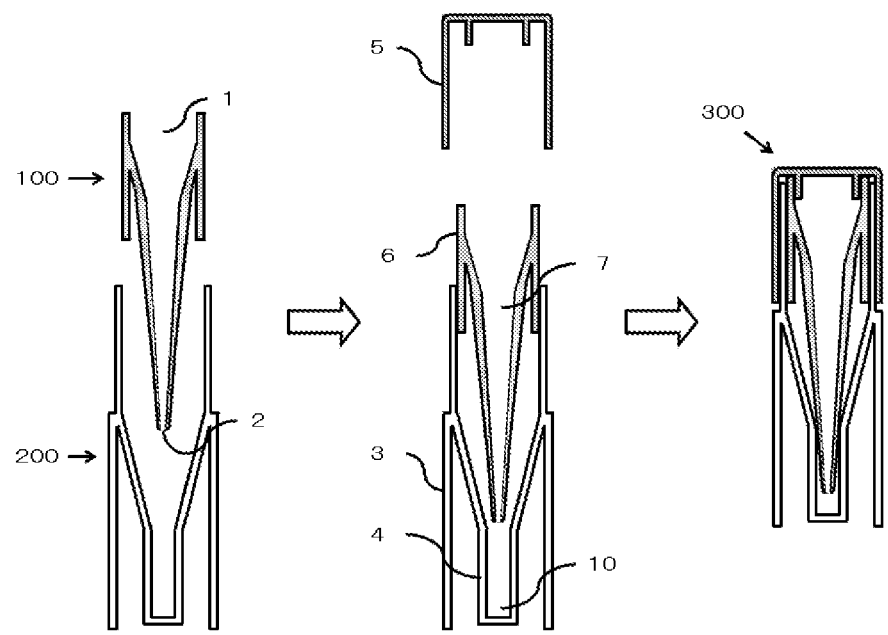
FIG. 6 is a view showing a schematic plan view of the sample collection and separation device of the third embodiment comprising the sample collection unit and the analyte storage unit according to the present invention, and showing the way of using the sample collection unit and the analyte storage unit.

FIG. 6 is a view explaining the sample collection and separation device 300 of the third embodiment according to the present invention. Like in the first embodiment, for the analyte storage unit main body 3 carrying the sample collection unit 100 inserted therein, a sample in the sample collection unit is sealed by the sample collection unit bottom cap 4 and the analyte sealing cap 5, and centrifugation and storage or transportation are possible. In this situation, sealing of the bottom opening of the sample collection unit is attained by close adhesion of the end peripheral part of the sample collection unit with the inner side of the bottom cap 4, and also in the third embodiment, sealing of the opening may be attained by close adhesion of the end of the sample collection unit with the basal plane of the bottom cap, like in the first embodiment.

In any embodiment of the sample collection and separation device 300 of the present invention, information for identifying the sample collection and separation device 300 may be imparted to the analyte storage unit 200 or the analyte sealing cap 5, if there is no influence on the collection part. For example, a seal having ID printed thereon for identifying the sample collection and separation device 300, a one-dimensional bar cord produced based on the ID or the like is posted on the analyte sealing cap 5, resulting in that information can be imparted to the sample collection and separation device 300 after collection or before collection.

In the sample collection unit 100, a sample collection unit body 6 has a sample collection portion 7 of hollow structure having capillary function, and the hollow penetrates between both ends of this sample collection portion 7 and openings are present at the top and the bottom, and a sample can be collected through any of the top opening 1 or the bottom opening 2, and it is preferable that a sample is collected through the bottom opening in such a sample collection unit of the present invention, and by this, a target amount of a sample can be collected easily. The sample collection portion 7 is sealed by the sample collection unit bottom cap 4 and the analyte sealing cap 5.

In the inside of the sample collection portion 7, the hollow structure has a gradient and has a structure in which the diameter of the end (lower part) is smaller than that of the upper part. By this gradient structure, suction of a sample is promoted by induction of negative pressure by flow of fluid in addition to capillary action in collecting a sample through the lower part, and a sample in the sample collection unit can be recovered through the opening at the upper part after centrifugation, storage and transportation.

For the sample collection portion 7, both ends are communicated and inside of the sample collection portion has capillary action and a function of negative pressure by flow of fluid, and the external form, the internal form and the material thereof are not restricted providing the sample collection means can be inserted into the diameter, and a better function of capillary action can be attained by using a hydrophilic or hydrophilized material on the inner surface.

For the sample collection unit body 6 having the sample collection portion 7, the material and the shape are not particularly restricted, and a hard material is preferable in consideration of a grasping property by an operator.

Particularly preferable, a portion extending from the bottom opening toward the upper direction in the sample collection portion and holding a sample after collection (hereinafter, referred to as "sample holding portion" in the present specification) forms the same shape as that of a sample suction portion of a pipette tip in which its inner diameter increases continuously.

The volume of the sample holding portion is preferably 200 μL or less, more preferably 150 μL or less, further preferably 100 μL or less. More specifically, the structure of the sample holding portion can take the same shape as that of a sample suction portion of a tip of a micro pipette, for example, 200 μL tip.

The inner diameter of the bottom opening of the sample collection unit 100 and the inner diameter of the body portion can be arbitrarily determined as long as the effect of capillary action is obtained. For example, the inner diameter of the bottom opening of the sample collection unit 100 is, for example, 0.1 mm or more and less than 2.0 mm, preferably 0.3 mm or more and less than 1.0 mm, but the inner diameter is not limited in this range. By this, a sample can be easily collected through the bottom opening, owing to capillary action.

The sample collection unit is preferably made of polymer compound material such as polyvinyl chloride, polyethylene, polypropylene, acrylonitrile butadiene styrene (ABS), polycarbonate, polyethylene terephthalate and the like, from the standpoint of workability, operability and the like.

The above exemplified materials are not compatible with water. Therefore, a tip of a micro pipette intending suction of a solution before discharge thereof, motivity for suction and discharge is separately used, and hydrophobicity on the surface of a tip material can impart high water drain in discharging the sucked solution. However, in the case of sucking a sample by utilizing capillary action, this nature is not preferable, therefore, it is preferable that the inner wall of the sample holding portion is hydrophilized in the present invention. If the inner wall is not hydrophilized, when blood is used as a sample, blood does not flow in smoothly. Because of a combination of capillary action and the effect of hydrophilization of the inner wall, a target amount of blood can be collected easily.

Hydrophilicity of the inner wall of the sample holding portion can be imparted, for example, by forming a porous structure on the surface of the inner wall by a chemical treatment such as etching, chemical vapor deposition and the like, or by introducing a hydrophilic functional group onto the surface of the inner wall via a catalyst, but the method is not limited to them. Treatments of imparting hydrophilicity to the surface of a material composed of a polymer compound, for example, polypropylene and polycarbonate, is known, and these methods can be used. It is possible to use, for example, a method of using a mixed gas of a fluorine gas and an oxygen gas and a technology described in ENOMOTO Hidehiko, MURATA Toshiya, Surface Technology ("HYOMEN-GIJYUTSU"), Vol. 59, No. 5, p. 282-287 (2008), but the method is not limited to them.

For the analyte storage unit main body 3, the shape thereof is not limited and the material thereof also is not limited providing the sample collection unit 100 can be inserted therein. A highly transparent hard material is preferable in view of recovering of a sample by an operator, a grasping property, transportability and the like.

For the bottom cap 4 for the sample collection unit, the shape and the material thereof are not limited providing the end (lower part) of the sample collection unit 100 can be sealed, however, it is necessary to enhance the degree of sealing for preventing elution in centrifugal separation and drying of an inner sample.

The shape of the bottom cap 4 for the sample collection unit is not particularly restricted providing the end (lower part) of the sample collection unit 100 can be sealed, and in addition to a flat shape, it is preferable to have a lock mechanism 9 for holding the end (lower part) of the sample collection unit 100 and/or an agent holding portion 10 for holding an agent which is added depending on the target sample on the base. A protrusion adjusted to the diameter of the end of the sample collection unit may also be provided on the base of the bottom cap 4.

The lock mechanism 9 is provided for the purpose of enhancing the degree of sealing of the lower part of the sample collection unit 100 with the bottom cap 4 and preventing detachment of the sample collection unit 100. For the lock mechanism, the setting position thereof on the bottom cap is not limited and the structure thereof is also not limited providing the object can be attained. It is possible to attain the object by, for example, providing stepped and accordion-like structures on the sample collection unit 100 and the bottom cap 4 so that the sample collection unit 100 is locked when it is pushed down.

The agent holding portion 10 is provided for the purpose of providing an agent to be added depending on a target sample. For example, it is envisaged that an anticoagulant is previously added for obtaining plasma, in the case of a blood sample, and additionally, an agent such as a separating agent and the like may also be added for the purpose of improving preservation stability of serum or plasma after centrifugation. If an agent holding portion is provided in the sample collection unit bottom cap and a separating agent is previously filled in, when a sample collection unit having collected a sample is inserted into an analyte storage unit, the separating agent flows into the sample collection unit, then, the end of the sample collection unit is sealed. By this, a sample containing the separating agent added can be prepared without separately adding the separating agent. The volume of the agent holding portion 10 is not limited and also the structure thereof is not limited providing sealing of the sample collection unit 100 can be attained. Sealing of a sample can be successfully attained by providing the lock mechanism 9. The agent holding portion 10 can be provided in any of the first embodiment, the second embodiment and the third embodiment described above.

For the analyte sealing cap 5, the shape and the material thereof are not particularly limited providing sealing of the upper part of the sample collection portion in the sample collection unit is possible. It may also be integrated with the sample collection unit 100 or the analyte storage unit for preventing loss.

The analyte sealing cap 5 is configured so that it can be arbitrarily removed or opened or closed, and by this mechanism, a sample collection means 15 described later can be easily inserted. Further, an additional sealing cap may be provided on the analyte sealing cap 5. By such a configuration, for example, the upper part of the sample collection portion 7 in the sample collection unit is sealed and a sample (an analyte) is centrifugally separated, then, the sealing cap 5 is opened again, and the centrifugally separated supernatant (serum or plasma 12, when the analyte is blood) can be recovered. Thus recovered serum or plasma 12 is a material suitable for blood analysis since the serum or plasma 12 is the same as the serum or plasma prepared by collecting blood using a syringe and the like and performing centrifugation.

It is also possible to provide an additional cap which can be opened and closed for inserting a sample collection means shown below, above the analyte sealing cap 5.

Collection of a sample using the sample collection unit 100 will be illustrated with reference to FIG. 7.

Figure 7:
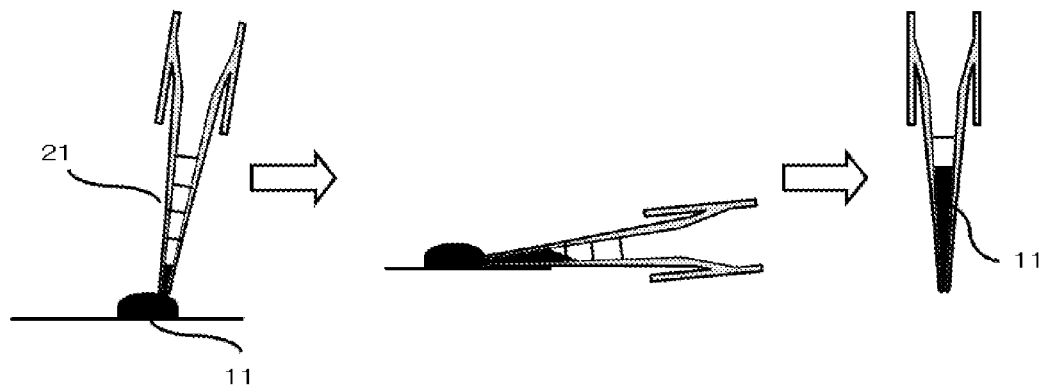
FIG. 7 is an explanation view of an embodiment of collecting a sample through the lower part, by using the sample collection unit.

In conducting collection of a sample, a sample 11 is allowed to contact with the lower part of the sample collection portion 7 as shown in FIG. 7, as a result, sucking of a sample starts owing to capillary action or negative pressure generated by flow of fluid, and a sample is sucked and filled in the sample collection portion 7. In FIG. 7, the sample collection unit 100 is inclined horizontally, and by this arrangement, a larger amount of a sample can be collected more easily. However, it is not necessary to be inclined when collection of a target amount of a sample is possible.

The amount of a sample to be collected can be changed depending on the target examination and measurement, and the length and the diameter of the sample collection portion 7 can be adjusted correspondingly. For example, the amount of a sample to be collected can be adjusted in the range of 10 μL to 300 μL, preferably 10 μL to 200 μL, further preferably 50 μL to 100 μL, but the amount is not limited in this range.

Collection of a specific amount of a sample can be conducted accurately, by providing a guide line 21 indicating collection of a specific amount in the sample collection unit. Further, measurement of hematocrit is also possible by converting the amount of blood cells by the guide line 21, after centrifugation.

A method of separation of serum or plasma and blood cells by centrifugation will be illustrated with reference to FIGS. 8 to 11.

Figure 8:
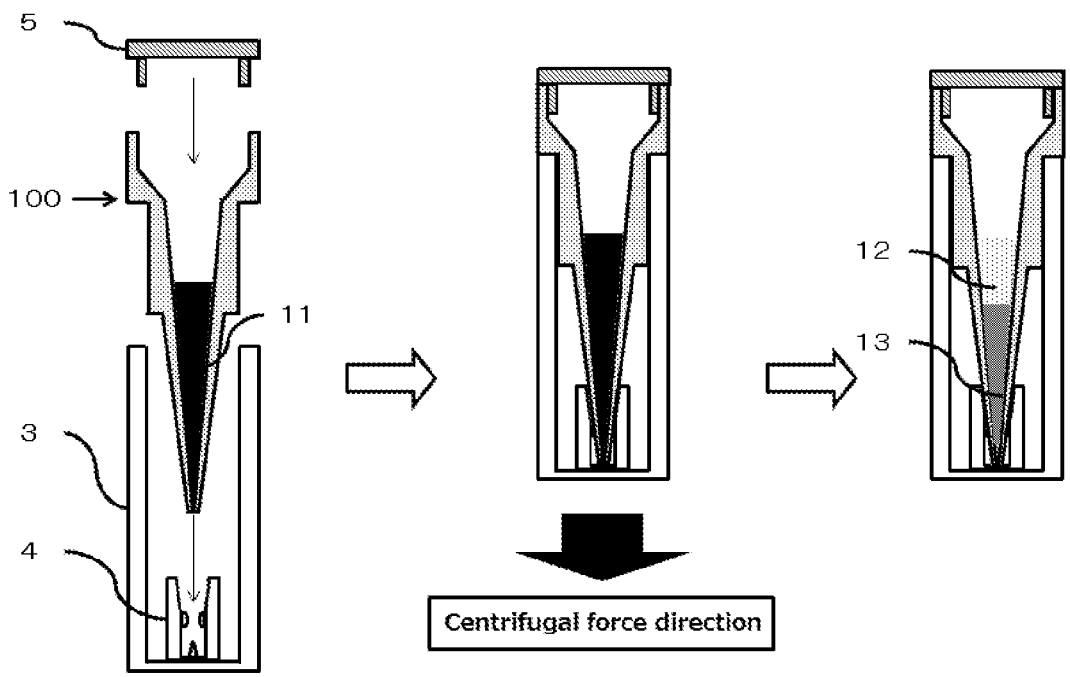
FIG. 8 is an explanation view showing a centrifugation method of a collected sample, using the sample collection and separation device of a first embodiment. In this situation, the bottom opening of the sample collection unit is sealed by close adhesion of the end part of the sample collection unit with the basal plane of the bottom cap, and in some cases, further with a protrusion.

FIG. 8 shows an embodiment in which a separating agent is not previously added into an agent holding portion, and a protrusion 19 is provided on the base of the sample collection unit bottom cap 4. Even if the protrusion is not present, sealing of the opening at the end of the sample collection unit can be attained by close adhesion of the base of the bottom cap 4 with the end of the sample collection unit 100 or by close adhesion of the inner side surface of the bottom cap 4 with the end peripheral outer surface of the sample collection unit 100. The sample collection unit 100 filled with a sample 11 by a sample collection method already described is inserted into the analyte storage unit main body 3, the lower part of the sample collection unit is sealed with the bottom cap 4, and further, the sample collection unit 100 is sealed by the analyte sealing cap 5, then, the sample is separated into serum or plasma 12 and blood cell 13 by centrifugation, and under this condition, the device can be stored or transported.

Figure 9:
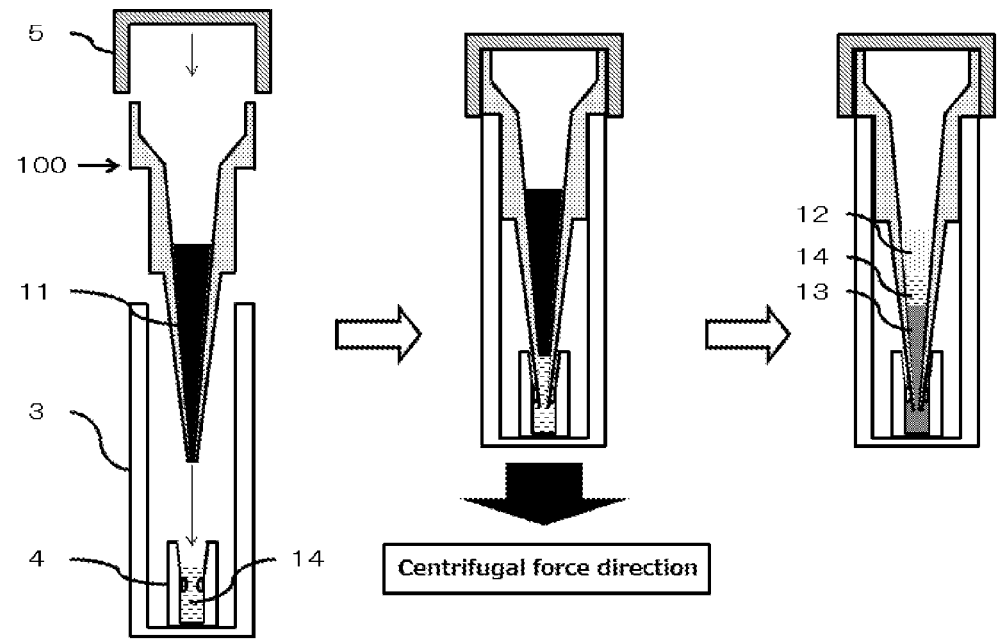
FIG. 9 is an explanation view showing a method of inserting the sample collection unit and a method of centrifuging a collected sample, using the sample collection and separation device of a second embodiment, when a separating agent is added into an agent holding portion provided in the bottom cap. In this situation, when the sample collection unit is inserted, close adhesion is formed between the end peripheral part of the sample collection unit and the inner side of the bottom cap and the separating agent flows into the sample collection unit through the bottom opening of the sample collection unit, and a sample containing the separating agent added is prepared. Thereafter, centrifugation is conducted to cause separation of components with the separating agent as the boundary.
Figure 10:
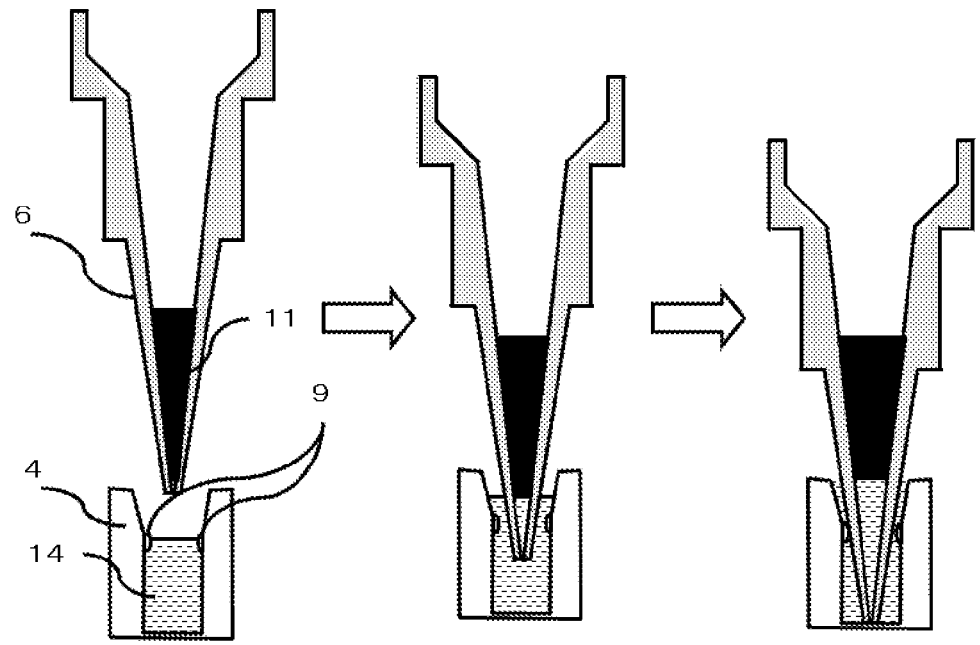
FIG. 10 is a view enlarging the structure of the agent holding portion of the sample collection and separation device shown in FIG. 9.
Figure 11:
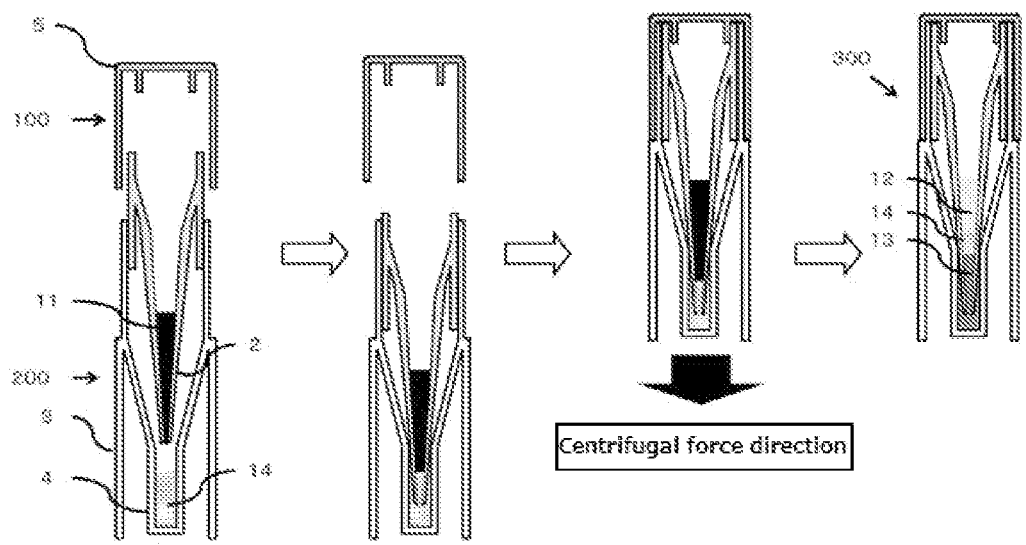
FIG. 11 is an explanation view showing a method of inserting the sample collection unit and a method of centrifuging a collected sample, using the sample collection and separation device of a third embodiment, when a separating agent is added into an agent holding portion. In this situation, when the sample collection unit is inserted, close adhesion is formed between the end peripheral part of the sample collection unit and the inner side of the bottom cap and the separating agent flows into the sample collection unit through the bottom opening of the sample collection unit, and a sample containing the separating agent added is prepared. Thereafter, centrifugation is conducted to cause separation of components with the separating agent as the boundary.

Further, an embodiment in which a separating agent is previously added to an agent holding portion will be illustrated with reference to FIGS. 9 to 11. FIG. 10 is a view enlarging the structure of the agent holding portion of the sample collection and separation device shown in FIG. 9.

In the figure, an agent holding portion 10 is provided on the bottom cap 4 for the sample collection unit, and a separating agent 14 is previously filled in the portion. When the sample collection unit 100 is pushed down to the agent holding portion 10 filled with the separating agent 14, close adhesion is formed between the end peripheral part of the sample collection unit 100 and the inner side of the bottom cap 4, and the separating agent 14 flows into the sample collection portion 7 through the bottom opening of the sample collection unit, and a sample containing the separating agent added is prepared. When the sample collection unit containing the separating agent as described above is subjected to centrifugation, the blood cell 12 transfers to the agent holding portion 10, and the separating agent 14 transfers to a position between the serum or plasma 12 and the blood cell 13. By this, mixing of the serum or plasma 12 and the blood cell 13 can be prevented, and excellent preservation stability is obtained over a long period of time.

When the sample collection unit is inserted into the agent holding portion containing a separating agent, it is preferable to make a structure of the agent holding portion letting the separating agent escape along the side wall of the sample collection unit, so that excess pressure is not applied to the sample in the sample collection unit until the lock mechanism adhere closely to the side wall of the sample collection unit. That is, if the structure is not fitted with a gradient continuing from the bottom opening of the sample collection unit, excess pressure is applied to a sample until the lock mechanism adheres closely to the side wall of the sample collection unit, consequently, the sample, for example, blood cells are broken or hemolyzed, and the side wall of the sample collection unit does not reach the lock mechanism, in many cases.

In the present invention, the kind, the material and the like of the separating agent which can be used are not particularly limited, and for example, those composed of silicon, α-olefin-maleate, polyester polymers, acrylic polymers, chlorinated polybutene, cyclopentadiene resins, and modified cyclopentadiene resins prepared by introducing a hydroxyl group, an ester group, an ether group, an epoxy group and the like in cyclopentadiene resins, as the main component, are listed.

In an embodiment of adding an anticoagulant in the present invention, coagulation of the blood cell 13 is inhibited by an anticoagulant, therefore, storage or transportation under condition directly after collection is possible even if separation of plasma and the blood cell 13 by centrifugation is not conducted. It is also possible to separate plasm and blood cell by conducting centrifugation.

In addition, addition of an agent which is used depending on the target sample and examination can be attained by previously adding an agent into the agent holding portion 10.

The kind, the material and the like of the agent which can be used in the present invention are not particularly limited, and the anticoagulant includes, for example, an alkali metal salt of ethylenediaminetetraacetic acid (EDTA), an alkali metal salt of heparin, sodium citrate, and the like.

Collection of a sample after centrifugation will be illustrated with reference to FIGS. 12 to 14.

Figure 12:
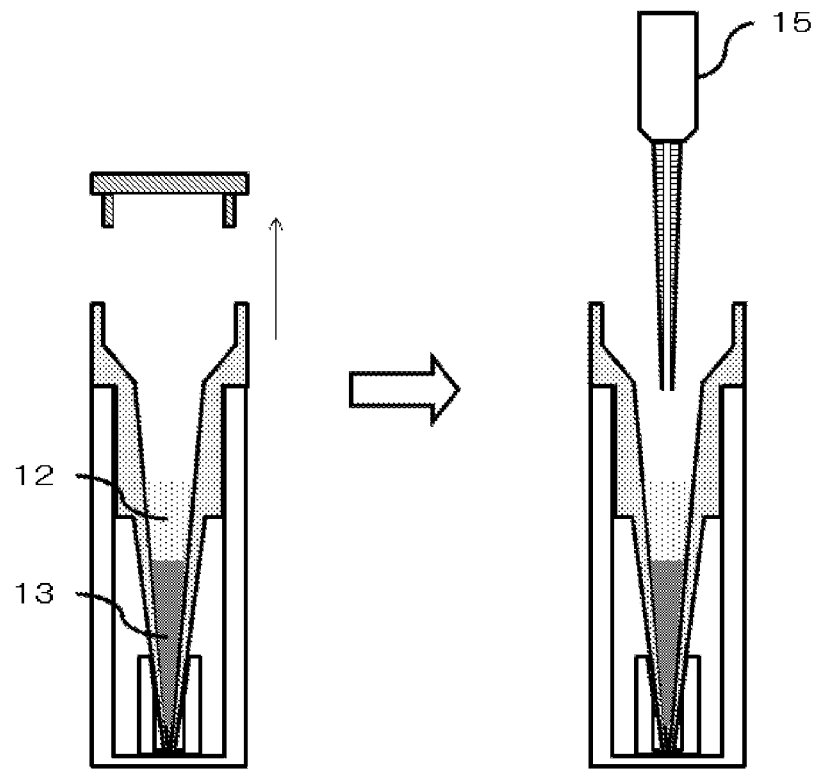
FIG. 12 is an explanation view showing a sample collecting method after centrifugation, using the sample collection and separation device of the first embodiment.
Figure 13:
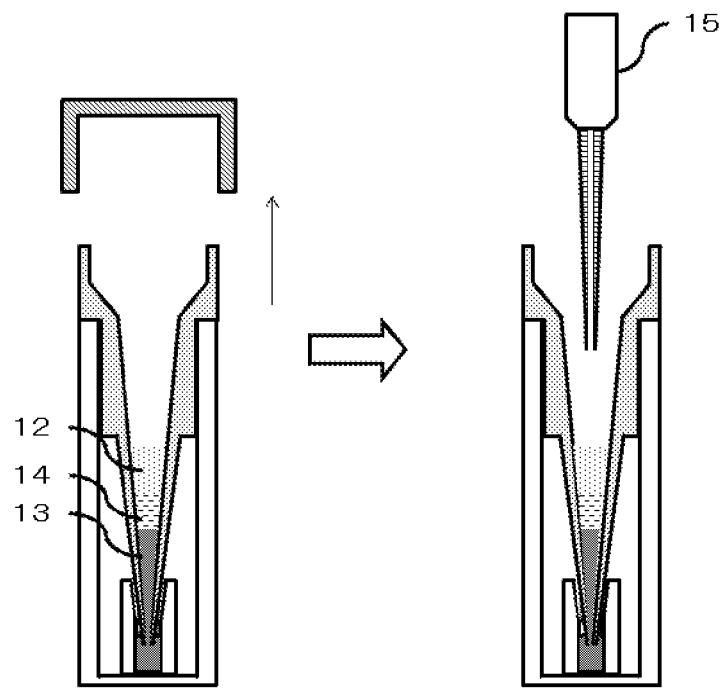
FIG. 13 is an explanation view showing a sample collecting method after centrifugation, using the sample collection and separation device of the second embodiment.
Figure 14:
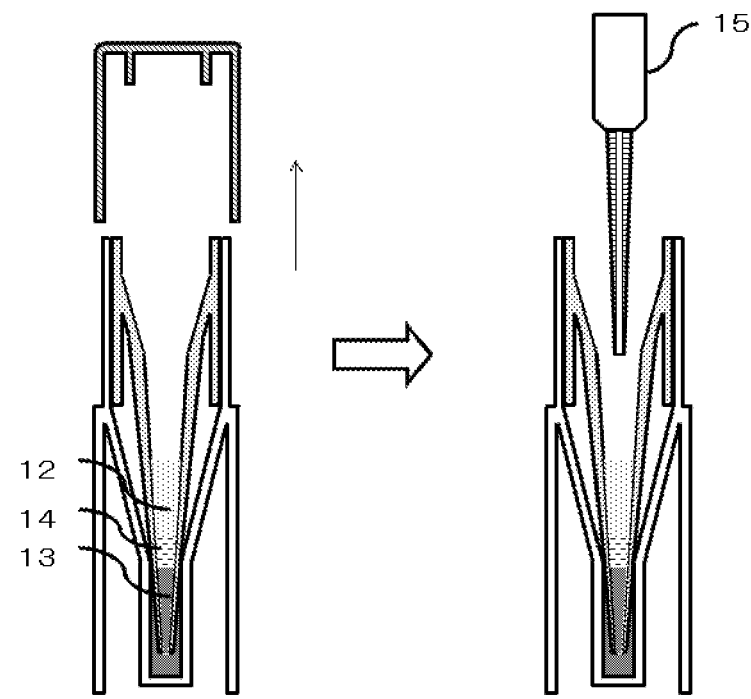
FIG. 14 is an explanation view showing a sample collecting method after centrifugation, using the sample collection and separation device of the third embodiment.

As shown in FIGS. 12 to 14, the separated serum or plasma 12 and blood cell 13 are, if necessary, preserved or transported, then, the sealing cap 5 is released and the target sample is recovered by the sample collection means 15, and analyzed according to an ordinary method. The sample collection means 15 is not restricted providing it can access into the sample collection portion 7, and for example, quantitative collection is possible by using a micro pipette and a pipette tip, and additionally, for example, by coloring the separating agent, the sample separation surface can be detected automatically, and collection by an automatic dilutor which can collect only a sample is possible.

As another embodiment of the present invention, in a sample needing no centrifugation or a sample requiring centrifugation after transportation, it is possible to preserve and transport a collected sample after sealing with an analyte sealing cap.

By using the sample collection unit of the present invention, even a 200 μL or less of a sample can be simply collected by a hollow structure in the sample collection unit, and serum or plasma and blood cell can be recovered without waste by conducting centrifugation without transferring of a collected sample.

When the sample collection and separation device of the present invention is used, even a very small amount of peripheral blood collected form fingertip or earlobe and the like can be prepared into an excellent sample suitable for blood analysis. When diluted, such a sample can be analyzed according to a conventional protocol and an existing analysis apparatus which is used for analysis of brachial vein blood collected by a conventional blood collecting tube and the like. That is, the same blood analysis as conventional one can be conducted using a very small amount of peripheral blood collected from fingertip or earlobe and the like.

For example, if 50 μL of whole blood is collected from fingertip and serum or plasma is prepared using the sample collection and separation device of the present invention, about 20 μL of serum or plasma can be obtained, though the method is not limited to this. If this is diluted 10-fold with a dilution buffer solution (for example, physiological saline), 200 μL of a sample is prepared. By using this sample, usual blood biochemical analysis can be conducted.

That is, the present invention also provides a sample collection and separation device which can be used for conducting blood analysis using a very small amount (for example, 200 μL or less, preferably 100 μL or less, more preferably 50 μL or less) of peripheral blood collected from fingertip or earlobe and the like. For example, blood collected using the sample collection and separation device of the present invention can be used in examinations of general biochemical items and/or immune items usually used in blood tests, what is called, blood biochemical examinations, and further, also for special examination items such as cancer markers and allergy.

EXAMPLES

The present invention will be illustrated by examples below, but the present invention is not limited to the following examples.

Example 1: Comparison of Result of Biochemical Examination Between Serum Collected by Sample Collection and Separation Device of the Present Invention and Serum Collected by Usual Means 1. Method Serum Collected by Sample Collection and Separation Device of the Present Invention (Very Small Amount of Serum):

Using a sample collection and separation device of the present invention, peripheral blood (by lancet tap) was filled in a sample collection unit, it was inserted into an analyte storage unit, centrifugation (1800×G, 10 min) was conducted and plasma was collected from the upper part of the sample collection unit. Further, the collected plasma was diluted 10-fold with physiological saline.

Usually Blood-Sampled Serum (Original Serum):

Brachial vein blood was centrifugally separated in an experimental tube. Values of 13 general biochemical examination items for the collected serums were compared.

In the examinations, JEOL-BM6050 (JEOL) was used and reagents for measurement manufactured by DENKA SEIKEN Co., Ltd. were used.

The examination items performed are as described below.

1) TP (total protein), 2) ALB (albumin), 3) ALT (GPT), 4) AST (GOT), 5) TC (total cholesterol), 6) TG (neutral fat), 7) LDL, 8) HDL, 9) BUN (urea nitrogen), 10) CRE (creatinine), 11) UA (uric acid), 12) γ-GTP 2. Result As shown in Table 1 (comparison of analysis of vein blood and fingertip very small collected blood diluted liquid), it was confirmed that there is a very good correlativity between measured values of serum (micro test value) collected by the sample collection and separation device of the present invention and measured values of blood (original serum value) collected by a usual blood collection means.

TABLE 1

| | | | #001 | | #002 | | #003 | | #004 | | #005 | |
|---|---|---|---|---|---|---|---|---|---|---|---|---|
| | Not particular | | Original | Micro | Original | Micro | Original | Micro | Original | Micro | Original | Micro |
| Test Item | Lower limit | Upper limit | Serum value | test Value | Serum value | test Value | Serum value | test Value | Serum value | test Value | Serum value | test Value |
| Total protein | 6.5 | 8.0 | 8.2 | 8.3 | 7.6 | 7.7 | 7.3 | 7.3 | 7.3 | 7.2 | 7.8 | 7.9 |
| Albumin | 4.0 | — | 4.2 | 4.1 | 4.4 | 4.5 | 4.3 | 4.2 | 4.6 | 4.5 | 4.5 | 4.7 |
| Creatinine | — | 1.00 | 1 | 0.9 | 0.8 | 0.9 | 1.00 | 0.9 | 0.70 | 0.70 | 0.8 | 0.70 |

TABLE 1-continued

|  | Not particular | | #001 | | #002 | | #003 | | #004 | | #005 | |
|---|---|---|---|---|---|---|---|---|---|---|---|---|
|  | | | Original | Micro | Original | Micro | Original | Micro | Original | Micro | Original | Micro |
| Test Item | Lower limit | Upper limit | Serum value | test Value | Serum value | test Value | Serum value | test Value | Serum value | test Value | Serum value | test Value |
| Urea nitrogen | 9 | 21 | 13 | 14 | 16 | 18 | 20 | 22 | 16 | 17 | 13 | 18 |
| Uric Acid | 2.1 | 7.0 | 9.0 | 9.0 | 7.4 | 7.6 | 4.9 | 4.8 | 4.1 | 4.2 | 5.7 | 5.9 |
| Total cholesterol | 140 | 199 | 247 | 242 | 236 | 243 | 197 | 194 | 209 | 209 | 175 | 177 |
| HDL cholesterol | 40 | 119 | 53 | 51 | 88 | 91 | 68 | 67 | 67 | 66 | 65 | 64 |
| LDL cholesterol | 60 | 119 | 201 | 198 | 129 | 131 | 110 | 113 | 137 | 140 | 99 | 103 |
| Neutral fat | 30 | 149 | 102 | 99 | 252 | 255 | 148 | 142 | 58 | 61 | 76 | 83 |
| AST | 0 | 30 | 18 | 19 | 24 | 26 | 22 | 24 | 29 | 30 | 17 | 21 |
| ALT | 0 | 30 | 24 | 26 | 22 | 25 | 19 | 20 | 42 | 44 | 14 | 17 |
| γ-GTP | 0 | 50 | 70 | 68 | 49 | 48 | 26 | 24 | 21 | 21 | 18 | 17 |
| Fasting blood glucose | 70 | 110 | 133 | 131 | 171 | 175 | 123 | 127 | 78 | 80 | 137 | 142 |

Example 2: Hydrophilization Treatment of Inner Wall of Sample Collection Unit With Surfactant In a sample collection unit having an end internal diameter of 0.48 mm formed of polycarbonate, water mixed with a red dye (about 10 mg of a food dye (dextrin 85%, Food Red No. 102 15%) was added to 200 ml of tap water) or human blood obtained from fingertip by a lancet was tried to be sucked into the sample collection unit by capillary action. The suction was impossible in either case. In contrast, after rinsing the inside of the sample collection unit with a commercially available detergent containing a surfactant (about 2 ml of a commercially available neutral detergent (surfactant 31%) was added to 200 ml of tap water), each 100 µL or more of the water and the human blood could be sucked according to visual observation.

These results suggest that the surfactant was adsorbed to the inner surface of the sample collection unit and surface wettability inside of the sample collection unit was improved, namely, hydrophilicity was enhanced.

Blood was sucked by the sample collection unit treated with the surfactant, then, subjected to centrifugation (1800×G, 10 min), to find slight reddening of a serum portion, thus, it was supposed that red blood cell components were broken or hemolyzed by the surfactant.

Example 3: Hydrophilization Treatment of Inner Wall of Sample Collection Unit by Etching A sample collection unit having an end diameter of 0.48 mm formed from ABS was immersed in a solution containing hexavalent chromium for 12 minutes, intending induction of capillary action, thereby, butadiene on the surface of ABS was dissolved and etching holes were made on the surface, to form a fine porous structure. Sucking was conducted in the same manner as in Example 2.

As a result, water mixed with a red dye and human blood obtained from fingertip by a lancet were sucked in an amount of only about 20 µL at the end of the tip.

Further, when the above-described etching treatment time was doubled, both the dye mixed water and the blood could be successfully sucked in an amount of 100 µL or more.

Example 4: Hydrophilization Treatment of Inner Wall of Sample Collection Unit With Mixed Gas of Fluorine Gas and Oxygen Gas For a sample collection unit having an end diameter of 0.48 mm formed of polycarbonate, a hydrophilization treatment by a fluorine gas treatment was entrusted to Takamatsu Teisan Co., Ltd. (Takamatsu city, Kagawa prefecture) based on the description of JP-A No. 2010-150460, and a surface modification treatment was conducted using a mixed gas of a fluorine gas and an oxygen gas under conditions of a fluorine gas partial pressure of 1.33 Pa, an oxygen gas partial pressure of 93100 Pa, a treatment temperature of 25° C. and a treatment time of 600 seconds.

In this fluorine treatment, hydrophilicity of a carboxyl group, a hydroxyl group and the like can be manifested by utilizing high reactivity of a fluorine gas and oxygen.

As a result, water mixed with a red dye and human blood obtained from fingertip by a lancet could be sucked in an amount of 100 µL by this tip. Further, when they were subjected to centrifugation (1800×G, 10 min), reddening of a serum portion was not observed and excellent serum could be obtained.

Example 5: Use of Sample Collection and Separation Device Previously Filled With Separating Agent A sample collection and separation device having an agent holding portion of the present invention was used. A sample collection unit bottom cap having the agent holding portion of the device was prepared and the portion was filled with a polyester gel (Nippon Becton Dickinson Company, Ltd.) as a separating agent. Thereafter, human blood obtained from fingertip by a lancet was collected in an amount of about 60 µL by using a sample collection unit of the device. The collected blood set in the device was subjected to centrifugation (1800×G, 10 min), to observe that the red blood cell part, the separating agent and the serum could be separated into three layers in this order.

The foregoing merely illustrates objects and subjects of the present invention, and does not limit the accompanying Claims. Without departing from the accompanying Claims, various modifications and alterations to the described embodiments will be apparent to those skilled in the art in view of the teachings herein.

EXPLANATION OF NUMERALS 1. sample collection unit top opening
2. sample collection unit bottom opening
3. analyte storage unit main body
4. sample collection unit bottom cap
5. analyte sealing cap
6. sample collection unit body 7. sample collection portion
9. lock mechanism
10. agent holding portion
11. sample
12. serum or plasma
13. blood cell
14. separating agent
15. sample collection means
19. protrusion
21. guide line
100. sample collection unit
200. analyte storage unit
300. sample collection and separation device

What is claimed is:

1. A blood sample collection and separation device, comprising
   a blood sample collection unit having an inside space specifically configured and structured to hold a blood sample and having openings at the top and the bottom, wherein the inside space, the bottom opening and the top opening communicate, the inner diameter thereof increases from the bottom opening toward the top opening, and the wall surface defining the inside space into which the blood sample is placed forms a gradient continuing from the bottom opening toward the top opening,
   an analyte storage unit having a housing into which the blood sample collection unit is inserted and having a blood sample collection unit bottom cap tightly sealing the bottom opening of the blood sample collection unit which is specifically configured and structured to hold the blood sample, wherein the blood sample collection unit bottom cap has an agent holding portion for holding an agent, and it is configured that when the blood sample collection unit is inserted into the analyte storage unit and the bottom opening is inserted into the agent holding portion, then, at least a part of the agent enters into the blood sample collection unit, and
   an analyte sealing cap for plugging the top opening of the blood sample collection unit, wherein when the analyte sealing cap plugs the top opening under condition of insertion of the blood sample collection unit into the analyte storage unit, the blood sample is sealed.

2. The blood sample collection and separation device according to claim 1, wherein a lock mechanism is provided in the agent holding portion, and it is configured that when the blood sample collection unit is inserted into the analyte storage unit and the bottom opening is inserted into the agent holding portion, then, the lock mechanism contacts with the end peripheral part of the blood sample collection unit and the blood sample is held sealed under condition of entering of at least a part of the agent into the blood sample collection unit.

3. The blood sample collection and separation device according to claim 2, wherein the wall surface is hydrophilized.

4. The blood sample collection and separation device according to claim 3, wherein an agent is previously placed in the agent holding portion of the analyte storage unit.

5. The blood sample collection and separation device according to claim 4, wherein the agent is a separating agent.

6. The blood sample collection and separation device according to claim 5, wherein the blood sample is peripheral blood.

7. The blood sample collection and separation device according to claim 3, wherein the blood sample is peripheral blood.

8. The blood sample collection and separation device according to claim 4, wherein the agent is an anticoagulant.

9. The blood sample collection and separation device according to claim 4, wherein the blood sample is peripheral blood.

10. The blood sample collection and separation device according to claim 2, wherein the upper part of the agent holding portion is in the form of taper.

11. The blood sample collection and separation device according to claim 2, wherein the blood sample is peripheral blood.

12. The blood sample collection and separation device according to claim 2, wherein an agent is previously placed in the agent holding portion of the analyte storage unit.

13. The blood sample collection and separation device according to claim 12, wherein the agent is a separating agent.

14. The blood sample collection and separation device according to claim 12, wherein the agent is an anticoagulant.

15. The blood sample collection and separation device according to claim 1, wherein the wall surface is hydrophilized.

16. The blood sample collection and separation device according to claim 15, wherein the blood sample is peripheral blood.

17. The blood sample collection and separation device according to claim 15, wherein the blood sample is peripheral blood.

18. The blood sample collection and separation device according to claim 1, wherein the blood sample is peripheral blood.

* * * * *